(12) United States Patent
Welling

(10) Patent No.: US 6,294,514 B1
(45) Date of Patent: *Sep. 25, 2001

(54) PROCESS FOR PREPARING MONO-LONG CHAIN AMINE OXIDE SURFACTANTS WITH LOW NITRITE, NITROSAMINE AND LOW RESIDUAL PEROXIDE

(75) Inventor: Stanley James Welling, Hamilton, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/200,391

(22) Filed: Nov. 24, 1998

(51) Int. Cl.[7] ................................. C11D 1/75; C11D 3/10; C11D 3/39
(52) U.S. Cl. .................... 510/503; 510/499; 510/509; 510/370; 510/372; 564/298; 564/2
(58) Field of Search ..................................... 510/499, 503, 510/509, 370, 372; 564/2, 298

(56) References Cited

U.S. PATENT DOCUMENTS

| 3,333,000 | 7/1967 | Albert et al. | 260/583 |
|---|---|---|---|
| 4,650,904 | 3/1987 | Fujita | 564/298 |
| 4,942,260 | 7/1990 | Laurenzo et al. | 564/298 |
| 4,960,934 | 10/1990 | Smith et al. | 564/298 |
| 5,223,644 | 6/1993 | Blezard et al. | 564/2 |
| 5,442,113 | 8/1995 | Blezard et al. | 564/2 |
| 5,466,870 | 11/1995 | Miller et al. | 564/298 |
| 5,498,373 | 3/1996 | Miller et al. | 252/546 |
| 5,498,791 | 3/1996 | Blezard et al. | 564/2 |
| 5,543,515 | 8/1996 | Koehler et al. | 540/604 |
| 5,583,258 | 12/1996 | Hawkins | 564/298 |
| 5,639,880 | 6/1997 | Muller et al. | 544/173 |
| 5,710,333 | 1/1998 | Bader et al. | 564/298 |

*Primary Examiner*—Gregory Delcotto
(74) *Attorney, Agent, or Firm*—Frank C. Turner; Jason J. Camp

(57) ABSTRACT

Mono-long chain amine oxide surfactants can be prepared containing active levels of greater than about 30%, by weight of amine, and with low nitrite and nitrosamine levels and low levels of residual hydrogen peroxide when oxidized under controlled temperature conditions in the presence of bicarbonate material present at levels less than about 2.5%, by weight of amine, and without the presence of phase-modifying solvents.

9 Claims, No Drawings

PROCESS FOR PREPARING MONO-LONG CHAIN AMINE OXIDE SURFACTANTS WITH LOW NITRITE, NITROSAMINE AND LOW RESIDUAL PEROXIDE

FIELD OF THE INVENTION

The present invention relates to an improvement in a chemical process for preparing mono-long chain amine oxide surfactants, whereby the active content of the surfactant is greater than about 30%, by weight of the amine, and nitrite, nitrosamine and residual hydrogen peroxide levels are suppressed.

BACKGROUND OF THE INVENTION

The preparation of mono-long chain amine oxide surfactants by the oxidation of tertiary amines is of considerable commercial interest. Such surfactants are widely used in commercial cleaning compositions, especially high sudsing dishwashing detergents. Such concentrated solutions are especially useful in formulating concentrated or "compact" liquid detergent compositions which are now favored by many consumers and generally contain lower amounts of water than conventional detergents. However, the formulation of mono-long chain amine oxide surfactants containing high levels, i.e., greater than about 30%, by weight of the amine, has proven to be a difficult problem to overcome. Typically, mono-long chain amine oxide surfactants containing above 30% active result in an unhandleable gel especially when a phase modifying solvent is not incorporated. Also, some sources of mono-long chain amine oxide surfactants may be contaminated with residual amounts of nitrite materials, especially inorganic nitrites. Contamination by such nitrites may be tolerable under many circumstances. For some uses however, the presence of nitrites may be undesirable, since they can react with other ingredients which may be present in the fully formulated detergent compositions.

U.S. Pat. No. 5,583,258, issued Dec. 10, 1996 to Hawkins describes an economical process for preparing concentrated (greater than 30%) free flowing aqueous amine oxide solutions having reduced levels of nitrites and nitrosamines, and achieving said free flowing properties without the use of phase-modifying solvents. In that process, tertiary amine and hydrogen peroxide are reacted in the presence of up to 2.5% alkali metal bicarbonate (based on weight of the amine). The reaction temperature is in the range of 40–100° C. and the ratio of hydrogen peroxide to amine is 95%–125% of stoichiometric. The Hawkins reference is silent with respect to residual levels of hydrogen peroxide.

It has now been found that the presence of even relatively small amounts of hydrogen peroxide (i.e. in excess of 50 ppm or so) in amine oxides used in formulation of liquid detergents can result in odor problems, especially if the liquid detergents contain diamine compounds such as diaminopentane, which is a very effective buffer for use in such compositions. Also, when used in formulation of liquid detergents containing enzymes to enhance cleaning, amine oxides containing such relatively small amounts of hydrogen peroxide can cause degradation of the enzymes.

It is an objective of the present invention to produce high active aqueous amine oxides having residual hydrogen peroxide levels of less than 50 ppm, as well as having suppressed levels of nitrites and nitrosamines, and having free flowing properties without the use of phase modifying solvents.

It is another objective of the invention to produce said amine oxides at minimal reaction time.

All documents referred to herein are incorporated by reference and all percentages and ratios are "by weight" unless specified otherwise.

SUMMARY OF THE INVENTION

The present invention relates to a process for preparing aqueous mono-long chain amine oxide surfactant compositions having an active content of 30% or more, wherein said process comprises:

A. forming an aqueous solution of bicarbonate, the amount of said bicarbonate being from about 0.3% to about 2.5% by weight of the amine used in subsequent StepB and wherein said bicarbonate is selected from the group consisting of alkali metal bicarbonates, alkaline earth metal bicarbonates, bicarbonate precursors, and mixtures thereof, B. adding a tertiary amine having the general formula:

wherein each $R^1$ and $R^2$ are $C_1$–$C_4$ alkyl or hydroxyalkyl groups; and $R^3$ is a $C_8$ to $C_{18}$ alkyl or alkenyl group; and C. oxidizing said amine with hydrogen peroxide to form the corresponding mono-long chain amine oxide having the general formula:

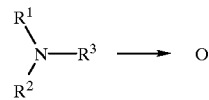

wherein $R^1$, $R^2$, and $R^3$ are defined as above; wherein the reaction exotherm is allowed to reach a temperature within the range of about 60° C. to about 70° C. and is then maintained within that range until the hydrogen peroxide level is 50 ppm or less and wherein said process is essentially free of any phase modifying solvent.

DETAILED DESCRIPTION OF THE INVENTION

In accordance with the present invention, it has been found that high active, free flowing aqueous amine oxide compositions having suppressed levels of nitrites and nitrosamines and very low levels of residual hydrogen peroxide can be prepared, while minimizing reaction time. The process of the present invention is an improvement over U.S. Pat. No. 5,583,258 in that in addition to achieving a free flowing, high active amine oxide composition with suppressed levels of nitrites and nitrosamines, the present process also enables the production of said compositions with minimal levels (less than 50 ppm) hydrogen peroxide at reduced reaction time.

The present invention relates to a process for preparing aqueous mono-long chain amine oxide surfactant compositions containing greater than 30% amine oxide, which comprises:

A. forming an aqueous solution of bicarbonate, the amount of said bicarbonate being from about 0.3% to about 2.5% by weight of the amine used in Step B, and wherein said bicarbonate is selected from the group consisting of alkali metal bicarbonates, alkaline earth metal bicarbonates, bicarbonate precursors, and mixtures thereof, B. adding a tertiary amine having the general formula:

wherein each $R^1$ and $R^2$ are $C_1$–$C_4$ alkyl or hydroxyalkyl groups;
and $R^3$ is a $C_8$ to $C_{18}$ alkyl or alkenyl group; and C. oxidizing said amine with hydrogen peroxide to form the corresponding mono-long chain amine oxide having the general formula:

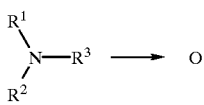

wherein $R^1$, $R^2$, and $R^3$ are defined as above; wherein the reaction exotherm is allowed to reach a temperature within the range of about 60° C. to about 70° C. and is then maintained within that range until the hydrogen peroxide level is 50 ppm or less and wherein said process is essentially free of any phase modifying solvent.

Mono-long chain amine oxide compositions produced by the present process contain greater than 30% amine oxide, typically 31% to 38%, preferably 32–37%.

Amine

The amines used as starting material in the present process have the following formula:

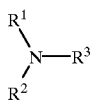

wherein each $R^1$ and $R^2$ are $C_1$–$C_4$ alkyl or hydroxyalkyl groups, preferably methyl groups, and $R^3$ is a $C_8$ to $C_{18}$, preferably a $C_{10}$–$C_{18}$, more preferably a $C_{12}$–$C_{16}$ alkyl or alkenyl group.

Hydrogen Peroxide

The oxidation step herein is conducted using hydrogen peroxide or a source of hydrogen peroxide, or hydrogen peroxide generated in situ. The oxidation is conducted in water. Hydrogen peroxide is commercially available in aqueous solutions of various strengths up to 90%, which makes it a convenient oxidizing agent for forming amine oxide solutions at the desired concentration.

Bicarbonate Material

The bicarbonate material is selected from the group consisting of alkali metal bicarbonates, alkaline-earth metal bicarbonates, ammonium bicarbonate, and mixtures thereof. It will also be understood that bicarbonate precursors can be used in place of bicarbonate salts, e.g., alkali metal carbonates can be used to generate bicarbonate in situ. Preferably said bicarbonate material is ammonium bicarbonate, and more preferably, sodium bicarbonate. The bicarbonate material is present at a level of from about 0.3% to 2.5%, by weight of amine, preferably at a level of from about 1% to about 2.1%, by weight of amine.

Process

The process is preferably carried out at a pH in the range of from about 7 to about 10, more preferably from about 8 to about 10.

Typically, amine oxide surfactants herein are produced by oxidizing the desired amine with hydrogen peroxide in the form of a 5% to 70% aqueous solution. The amount of hydrogen peroxide is typically from 100% to 115% of stoichoimetric to the amount of amine. Preferably, the hydrogen peroxide is used at about a 1% to 10% excess of the stoichoimetric amount.

The reaction can occur at temperatures of 40° C. to 100° C. However, in accordance with the present invention the initial reaction exotherm is controlled by application of cooling (and/or heat) until the reaction reaches 60° to 70° C., and then heat is provided, as needed, to maintain a 60° to 70° C. temperature throughout the remainder of the reaction. The hydrogen peroxide level is monitored and the reaction is considered complete when the hydrogen peroxide level reaches 50 ppm or less. Typically, when 100% to 115% of the stoichiometric level of hydrogen peroxide is used, the conversion of amine to amine oxide will be from about 95% to about 99.5%, with any residual hydrogen peroxide being decomposed to a resulting level of 50 ppm or less, preferably 40 ppm or less, more preferably 15 ppm or less by virtue of maintaining the above-specified reaction temperature. Reaction temperatures above about 70° C. can result in undesired by-products. Temperatures below about 60° C. will result in longer reaction times or the need to add reducing agents such as sodium sulfite to achieve the specified hydrogen peroxide level. Longer reaction times are economically undesirable. Likewise, the presence of residues of reducing agents in aqueous amine oxide compositions is undesirable. The compositions from the present process are free of said residues. Reaction times for the present process will typically be between 5 and 7 hours.

Conduct of the reaction in the present manner makes possible the production of high active (30% to 38%) aqueous amine oxide compositions with excellent flowability characteristics as well as minimal levels of hydrogen peroxide, and the low nitrite and nitrososamine levels described in the Hawkins '258 Patent described above. Typically the amine oxide compositions produced by the present process will have a nitrite content below about 3 ppm and a nitrosamine content below about 500 ppb. The present invention may be characterized as an improvement over the process of the Hawkins '258 patent wherein the improvement is the production of amine oxides having less than 50 ppm residual hydrogen peroxide and wherein said improvement is achieved by conduct of the process at a maintained temperature of 60°–70° C.

In the process of this invention the oxidation of the amine is carried out using otherwise conventional procedures, and can be conducted in a batch or multi-stage continuous manner. Monitoring of hydrogen peroxide level is done by standard sodium thiosulfate titration analysis.

EXAMPLE I

This example illustrates the difference between conduct of the oxidation of amine in the presence of bicarbonate, without the temperature control required by the present invention (Run A), compared to practice of the present invention (Run B).

In both cases the batch size is 1000 grams. The reactor is a 3000 milliliter glass vessel stirred with a Teflon blade at the end of a mixing shaft. The reactor is supported from above so that a cold water bath or electric heating mantle can be placed up around the bottom and sides of the reactor as needed to control temperature. The temperature is monitored by a thermometer immersed in the reaction materials. The water and sodium bicarbonate are added and mixed, the amine is weighed into the reactor and continuous agitation is begun. The temperature is adjusted as indicated for individual batches and the hydrogen peroxide is added. Reaction time is recorded from the addition of hydrogen peroxide.

In Run A the time-temperature profile was as follows:

Time 0:00-Temp is 25° C., Hydrogen peroxide is added to the mixture of aqueous bicarbonate and amine h./m. T 0:05–28° C.
0:10–31° C.
0:15–37° C.
0:21–45° C.
0:25–57° C.
0:28–68° C. raise water bath up around reactor
0:30–64° C. lower water bath
0:35–65° C.
0:40–64° C.
0:45–63° C.
0:50–61° C.
0:55–59° C., $H_2O_2$=1890 ppm
1:25–50° C.
2:55–35° C., $H_2O_2$=870 ppm
5:10,turn mixer off
24:00 (Approx.)—$H_2O_2$=470 ppm Run B was conducted in the same manner, except that when the temperature reached 60–70° C. it was maintained there throughout the entire reaction time, which was 6:00 hours. The experiment is summarized as follows:

|  | RUN A | RUN B |
|---|---|---|
| C12–16 Alkykdimethylamine (wt. %) | 35.0 | 35.0 |
| 49.5% $H_2O_2$ (Wt. %) | 11.1 | 11.1 |
| $NaHCO_3$ (wt. %) | 0.7 | 0.7 |
| Water (wt. %) | 53.2 | 53.2 |
| Molar % excess $H_2O_2$ used | 0.7 | 0.7 |
| Total batch time (Hrs.) | 24:00 | 6:00 |
| ppm $H_2O_2$ at end of batch | 470 | 40 |
| % free amine at end of batch | 0.17 | 0.23 |

In each case the product was a free flowing aqueous solutions at room temperature, containing approximately 37% amine oxide.

EXAMPLE II

The following are examples of hand dishwashing compositions utilizing amine oxide of the present invention.

TABLE 1

|  | A | B | C | D |
|---|---|---|---|---|
| AE0.6S[1] | 28.80 | 28.80 | 28.80 | 28.80 |
| Amine Oxide[2] | 7.20 | 7.20 | 7.20 | 7.20 |
| Citric acid | 3.00 | — | 3.00 | — |
| Maleic acid | — | 2.50 | — | 2.50 |
| Suds boosting polymer[3] | 0.22 | 0.22 | 0.22 | 0.22 |
| Sodium Cumene Sulfonate | 3.30 | 3.30 | 3.30 | 3.30 |
| Ethanol 40B | 6.50 | 6.50 | 6.50 | 6.50 |
| C11E9[4] | 3.33 | 3.33 | 3.33 | 3.33 |
| Diamine[5] | 0.55 | 0.55 | — | — |
| Diamine[6] | — | — | 0.55 | — |
| Diamine[7] | — | — | — | o.55 |
| Protease | — | — | 0.06 | 0.06 |
| Lipase | — | — | 0.05 | 0.05 |
| Perfume | 0.31 | 0.31 | — | — |
| Water | Bal. | Bal. | Bal. | Bal. |

[1]$C_{12-13}$ alkyl ethoxy sulfonate containing an average of 0.6 ethoxy groups.
[2]$C_{12-14}$ Amine oxide, containing approximately 40 ppm hydrogen peroxide.
[3]Polymer is (N,N-dimethylamino)ethyl methacrylate homopolymer.
[4]$C_{11}$ Alkyl ethoxylated surfactant containing 9 ethoxy groups.
[5]1,3 bis(methylamine)-cyclohexane.
[6]1,6-hexanediamine
[7]1,3 diaminopentane.

What is claimed is:

1. A process for preparing aqueous mono-long chain amine oxide surfactant compositions which contain more than 30% amine oxide wherein said process consists essentially of the steps:

A. forming an aqueous solution of bicarbonate, the amount of said bicarbonate being from about 0.3% to about 2.5% by weight of the amine of Step B, and wherein said bicarbonate is selected from the group consisting of alkali metal bicarbonates, alkaline earth bicarbonates, bicarbonate precursors, and mixtures thereof, B. adding a tertiary amine having the general formula:

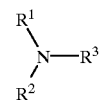

wherein each $R^1$ and $R^2$ are $C_1$–$C_4$ alkyl or hydroxyalkyl groups; and $R^3$ is a $C_8$ to $C_{18}$ alkyl or alkenyl group; and C. oxidizing said amine with hydrogen peroxide to form the corresponding mono-long chain amine oxide having the general formula:

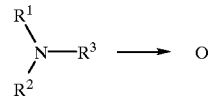

wherein $R^1$, $R^2$, and $R^3$ are defined as above; wherein of the reaction exotherm is allowed to reach a temperature within the range of about 60° C. to about 70° C. and is then maintained within that range until the hydrogen peroxide level is 50 ppm or less, and wherein said process is essentially free of any phase modifying solvent.

2. The process of claim 1 wherein the amine is a $C_{10}$–$C_{18}$ alkyl dimethyl amine.

3. The process according to claim 2 wherein the amine is a $C_{12}$–$C_{16}$ dimethylamine.

4. The process of claim 1 wherein the process is conducted at a pH of from about 7 to about 10.

5. The process of claim 1 wherein the bicarbonate material is selected from the group consisting of alkali metal bicarbonates.

6. The process of claim 5 wherein the bicarbonate is sodium bicarbonate.

7. The process of claim 5 wherein the amount of bicarbonate is from about 1% to about 2.1%, based on weight of the amine.

8. The process of claim 1 wherein the said mono-long chain amine oxide surfactant contains an active level of from about 31% to about 38% by weight.

9. The process of claim 8 wherein the active level of said surfactant is from about 32% to about 37% by weight of the composition.

* * * * *